US011484489B1

(12) United States Patent
Cornell et al.

(10) Patent No.: US 11,484,489 B1
(45) Date of Patent: Nov. 1, 2022

(54) SKIN CARE COMPOSITIONS AND METHODS FOR REGULATING SEBUM PRODUCTION

(71) Applicant: CODEX BEAUTY CORPORATION, San Jose, CA (US)

(72) Inventors: Marc Cornell, San Jose, CA (US); Barbara A. Paldus, San Jose, CA (US)

(73) Assignee: CODEX BEAUTY CORPORATION, San Jose, CA (US)

( * ) Notice: Subject to any disclaimer, the term of this patent is extended or adjusted under 35 U.S.C. 154(b) by 0 days.

(21) Appl. No.: 17/545,206

(22) Filed: Dec. 8, 2021

(51) Int. Cl.
| | |
|---|---|
| A61K 8/9722 | (2017.01) |
| A61Q 19/00 | (2006.01) |
| A61K 8/9711 | (2017.01) |
| A61K 8/9789 | (2017.01) |
| A61K 8/34 | (2006.01) |
| A61K 8/99 | (2017.01) |
| A61K 8/92 | (2006.01) |
| A61K 8/368 | (2006.01) |
| A61K 8/66 | (2006.01) |

(52) U.S. Cl.
CPC ............ *A61K 8/9722* (2017.08); *A61K 8/347* (2013.01); *A61K 8/368* (2013.01); *A61K 8/66* (2013.01); *A61K 8/92* (2013.01); *A61K 8/9711* (2017.08); *A61K 8/9789* (2017.08); *A61K 8/99* (2013.01); *A61Q 19/008* (2013.01)

(58) Field of Classification Search
None
See application file for complete search history.

(56) References Cited

U.S. PATENT DOCUMENTS

| | | | | |
|---|---|---|---|---|
| 10,721,937 | B1 * | 7/2020 | Cornell | A61K 8/368 |
| 2013/0195911 | A1 * | 8/2013 | Baier | A61Q 19/00 |
| | | | | 424/195.15 |
| 2014/0206842 | A1 * | 7/2014 | Majeed | C07K 7/06 |
| | | | | 530/345 |
| 2016/0206540 | A1 * | 7/2016 | Hood | A61K 8/69 |
| 2021/0330638 | A1 * | 10/2021 | Drennan | A61K 31/045 |

FOREIGN PATENT DOCUMENTS

FR   3029419   *   6/2016

OTHER PUBLICATIONS

Cho et al., "Inhibition of Inflammatory Responses by Centella asiatica via Suppression of IRAK1-TAK1 in Mouse Macrophages," The American Journal of Chinese Medicine 48(5):1103-1120 (2020).
Jamshidi et al., "The Clinical Efficacy and Safety of Tulsi in Humans: A Systematic Review of the Literature," Evidence Based Complement Alternative Medicine 2017:9217567 (2017). doi:10.1155/2017/9217567.
Lee et al., "Potential Role of the Microbiome in Acne: A Comprehensive Review," Journal of Clinical Medicine 8(7):987 (2019).
Sukketsiri et al., "ECa 233 Suppresses LPS-Induced Proinflammatory Responses in Macrophages via Suppressing ERK1/2, p38 MAPK and Akt Pathways," Biol Pharm Bull. 42(8):1358-1365 (2019).
Sun et al., "Therapeutic Potential of Centella asiatica and Its Triterpenes: A Review," Frontiers in Pharmacology 11:568032 (2020). doi: 10.3389/fphar.2020.568032.

* cited by examiner

*Primary Examiner* — David J Blanchard
*Assistant Examiner* — Sarah J Chickos
(74) *Attorney, Agent, or Firm* — Medler Ferro Woodhouse & Mills

(57) ABSTRACT

The present disclosure is directed to a composition for managing exaggerated sebum production in oily-prone skin, the composition containing: (1) a mixture of at least: (a) from about 0.02 to about 1% by weight of an ingredient capable of activating cannabinoid type-2 receptors ("$CB_2$"); (b) from about 0.1 to about 3% by weight of a blend of *Tetraselmis chuii* and *Fucus spiralis* algae extracts; (c) from about 0.1 to about 4% by weight of an extract of *Centella asiatica*; and (d) from about 0.01 to about 0.05% by weight of an extract of Tulsi, wherein all weights are based on total weight of the composition; (2) optionally, an emulsifier; and (3) a dermatologically acceptable carrier, wherein the composition has a pH ranging from about 4.5 to about 5.5.

29 Claims, No Drawings

SKIN CARE COMPOSITIONS AND METHODS FOR REGULATING SEBUM PRODUCTION

FIELD OF THE INVENTION

The present invention generally relates to compositions and methods of regulating sebum production in skin. More particularly, the invention is directed to the use of specific associations of plant-based extracts to arrive at efficacious compositions and methods for regulating exaggerated sebum production in order to inhibit disorders associated with oily skin, especially acne.

BACKGROUND

Sebaceous glands are small oil-producing glands present in the skin of mammals. They are annexed to hair follicles and produce sebum, which travels along the follicle to the skin where it can act as a moisturizing agent for the epidermis, helping to keep skin hydrated by sealing moisture therein.

Sebum is essentially a complex mixture of organic compounds, including squalene, triglycerides, aliphatic waxes, and cholesterol waxes. Sebum production in the sebaceous gland is carried out by terminally differentiated sebocytes whose metabolic activity is primarily directed toward lipid biosynthesis (lipogenesis) and fatty acid neosynthesis.

The fatty acids within sebum can be additionally supplemented by the bacterial residents of the skin microbiome carrying lipases, which convert triglycerides within sebum into free fatty acids.

Hyperseborrheic oily skin is characterized by exaggerated secretion of sebum. Conventionally, a sebum concentration greater than 200 µg/cm$^2$ measured on the forehead is characteristic of oily skin. Such skin is also often associated with a desquamation defect, a glistening complexion, and a thick skin grain, manifestations which are felt to be skin imperfections or aesthetic disorders.

In addition to its unsightly appearance, hyperseborrhea constitutes a condition in which complications can occur. It affects areas where there are many sebaceous glands and results mainly from an overstimulation of sebum production by these specific glands which contributes to the occurrence of acne vulgaris lesions.

Acne is a multifactor disorder affecting skin rich in sebaceous glands. It is the most common form of dermatosis. In its mildest form, dermatosis affects almost all human beings. Its frequency is at a maximum during puberty, but it can manifest itself at any age, affecting both men and women. Among its most common forms, mention may be made of comedonal acne, commonly known as juvenile acne, papulopustular and/or nodular acne, acne conglobata, and exogenous acne which appears as a reaction to inflammatory external factors.

More specifically, acne is a skin condition caused by the blockage or disruption of pilosebaceous units comprising the sebaceous gland and hair follicle. The following factors play a determining role in the formation of acne: genetic predisposition; overproduction of sebum (seborrhea); androgens; follicular keratinization disorders (including comedogenesis); bacterial colonization; and inflammatory factors.

Accordingly, the onset and severity of acne can be associated with different physiological and environmental factors. For example, the formation of a greater-than-normal number of keratinocytes in the deepest parts of the infundibular portion of the hair follicle (the hair follicle infundibulum) can be observed. These cells differentiate to give horny cells which gradually obstruct the lumen of the follicular canal. The physiological process of continuous desquamation of the acro-infundibulum (the superficial part of the hair follicle infundibulum) towards the surface is disturbed by the increased adhesion of the horny cells produced. A hyperkeratotic plug then forms, constituting the comedone, the initial lesion of acne.

Environmental factors can also play a large role in the development and severity of acne. For example, common residents of the skin microbiome, namely *Staphylococcus epidermidis* (*S. epidermidis*), *Malassezia furfur* (*M. furfur*), and *Cutibacterium acnes* (*C. acnes*, formerly called *Propionibacterium acnes*) find an ideal nutritive environment in the sebaceous follicle and can thrive in microaerophilic environments generated by plugged follicles. The alteration of the pilosebaceous environment due to the obstruction of the follicular canal as described above, and the improvement in the growth conditions for the native bacteria, can lead to infection and inflammation.

It is accepted that the lipases produced by residents of the skin microbiome dissociate the triglycerides within sebum to give free fatty acids. These free fatty acids can act as irritants to the follicular epithelium and subsequently stimulate hyper-proliferation. It can also initiate a localized proinflammatory response, attracting cells of the innate immune system. These immune cells migrate into the lumen of the follicle where they contribute to the enzymatic rupture of the follicle wall and development of the telltale pyogenic "whitehead" pimple.

The clinical manifestations observed may be of open or closed comedone types (e.g., microcyst, microcomedone, whitehead). The inflammatory lesions derived therefrom may be of papule or pustule type, with hardened nodules, abscesses, fistulae, and scarring. Thus, acneic and acne-prone individuals most commonly have oily skin, skin with an oily tendency, or combination skin (i.e., skin that is oily and/or tending to be oily). The skin of acneic or acne-prone individuals is most commonly shiny, with numerous imperfections present on the skin including microcysts, microcomedones, whiteheads, papules, pustules, hardened nodules, abscesses, fistulae, and scarring. The imperfections may also be of the type such as dull, muddy skin, dyschromia, redness, or rough skin with patches of dry skin. Cutaneous hyperkeratosis may be observed on the face with pores dilated, and skin being rough with a thick stratum corneum, giving the appearance of areas of dry skin in patches (epidermal atrophy and slight desquamation).

Consequently, hyperseborrhea (hyper secretion of sebum) is clearly a biological phenomenon that needs to be effectively inhibited to prevent the manifestation of associated skin disorders.

To combat hyperseborrhea, various compounds have been proposed which, when applied topically onto the skin, are intended to reduce lipogenesis in the sebocytes and, consequently, limit sebum production.

In addition to the production of sebum and its role in acne formation, microorganisms can affect and contribute to acne formation. The term "human microbiome" refers to all of the microorganisms that reside in, or on, the human body and that are believed to be 10× greater in number than the total number of cells comprising the human body. Recent studies have explored the role that the skin microbiome plays in the causation of acne. Advanced metagenomic sequencing has uncovered a significant difference in the population of microorganisms that make up the skin microbiome of acne-prone individuals versus acne-free individuals.

Acne is also believed to have a connection with a person's gastrointestinal tract, lending credence to the theory that the gut microbiome may be, in some way, also involved in the acne-formation process. As a result, there exists an ever-expanding body of research that is attempting to establish a causal connection between gut microorganisms, orally administered probiotics, and diet, together with their combined effect on acne formation, with the goal being the development of microbiome-based treatment therapies. See, e.g., Lee et al., "Potential Role of the Microbiome in Acne: A Comprehensive Review," J Clin Med. 2019 July; 8(7): 987.

Currently available acne treatments are not entirely satisfactory in terms of the side effects that are frequently associated with their use, such as irritant side effects with certain topical agents like retinoids and benzoyl peroxides, or even gastrointestinal side effects when oral antibiotic treatments are employed. In addition, resistance of C. acnes to certain local antibacterial treatments is frequently observed. Despite the plethora of active ingredient candidates available in the market, today's existing solutions for acne and oily-prone skin remain insufficient for many users seeking an effective solution for their skin condition with minimal side-effects.

Further adding to the above-mentioned challenge is a relatively recent phenomenon in the cosmetic industry. The industry has recently embraced a sub-category of products deemed to be organic/natural, and there is a current trend by consumers towards these types of goods. These products are believed to possess health and environmental benefits. Categories of these products include natural, green, clean, organic, holistic, sustainable, biodegradable, and eco-/environmentally friendly products. In line with the philosophy of such products, consumers expect them to also be preservative-free, paraben-free, phthalate-free, sulfate-free, silicone-free, synthetic fragrance-free, alcohol-free, phenoxyethanol-free, and non-toxic in general. This category of products has become one of the fastest growing in the global personal care and cosmetic segments.

The demand for such products, coupled with the lack of official standards for their certification, has led to much confusion among consumers as to what exactly qualifies as "natural" and/or "organic." Nevertheless, consumer awareness of what ingredients are believed to be acceptable has eliminated a bit of the confusion. As a result, consumers are gravitating towards products containing natural extracts, plant-based components, and ingredients derived from natural sources, while avoiding those products having ingredients that are either known to cause or suspected of causing adverse health reactions. This consumer trend has led to the private sector establishment of ethical and certified organic ingredients. A growing number of companies have recently implemented processes by which one can receive third-party certification of natural/organic products and ingredients.

One of the major deterrents associated with the use of plant-based ingredients in skin care compositions relates to their relative instability in products as evidenced by loss of potency, odor deviations, and discoloration. These negative attributes increase the risk of microbiological contamination and proliferation, instability, and safety of the products. This problem becomes even more acute when the composition has to be recognized by a regulatory agency or by consumers as being "natural," in which conventionally used synthetic and petroleum-derived ingredients are eliminated.

Formulating skin treatment products that are nature-based, highly efficacious, and stable, and contain components that are compatible with one another, without skin-sensitizing ingredients, can be a daunting challenge.

SUMMARY

The present disclosure provides cosmetic skin care compositions free of synthetic and petroleum-derived ingredients and methods that are effective at helping to control excess sebum production in order to proactively inhibit the occurrence of disorders associated with oily-prone skin, improve the appearance of acne-prone skin and diminish the appearance of acne.

The present disclosure is directed to a composition intended for application onto oily-prone skin, the composition comprising: (1) a mixture of at least (a) from about 0.02 to about 1% by weight of an ingredient capable of activating a cannabinoid type-2 receptor ("$CB_2$"); (b) from about 0.1 to about 3% by weight of a blend of *Tetraselmis chuii* and *Fucus spiralis* algae extracts; (c) from about 0.1 to about 4% by weight of an extract of *Centella asiatica*; and (d) from about 0.01 to about 0.05% by weight of an extract of Tulsi, all weights based on the total weight of the composition; (2) optionally, an emulsifier; and (3) a dermatologically acceptable carrier, wherein the composition has a pH ranging from about 4.5 to about 5.5.

According to yet another embodiment of the present disclosure, there is provided a composition intended for application onto oily-prone skin, the composition comprising: (1) a preservative system; (2) a mixture of at least (a) from about 0.02 to about 1% by weight of an ingredient capable of activating a cannabinoid type-2 receptor; (b) from about 0.1 to about 3% by weight of a blend of *Tetraselmis chuii* and *Fucus spiralis* algae extracts; (c) from about 0.1 to about 4% by weight of an extract of *Centella asiatica*; and (d) from about 0.01 to about 0.05% by weight of an extract of Tulsi, all weights based on the total weight of the composition; (3) optionally, an emulsifier; and (4) a dermatologically acceptable carrier, wherein the composition has a pH ranging from about 4.5 to about 5.5.

The present disclosure is also directed to a method of regulating sebum production in oily-prone skin in order to proactively inhibit the occurrence of disorders associated with oily-prone skin, improve the appearance of acne-prone skin and diminish the appearance of acne, by topically applying the above-disclosed compositions onto skin.

These and other features, aspects and advantages of the present disclosure will become evident to those skilled in the art from a reading of the present disclosure.

DETAILED DESCRIPTION

For purposes of the present disclosure, the use of the word "natural" is intended to encompass formulations that are plant-based, paraben free and contain less than about 5% by weight of synthetic ingredients in the formulation.

The skincare compositions of the present invention can comprise, consist essentially of, or consist of, the components of the present disclosure as well as other ingredients described herein. The term "comprising" as used herein is meant to include various optional, compatible components that can be used in the preservative systems and cosmetic compositions of the present disclosure. The term "consisting essentially of" as used herein means that the composition or component may include additional ingredients if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not, as well as the end points of that range. Further, these numerical ranges should be construed as providing support for a claim directed to any number or subset of numbers within that range or at the ends of that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice-versa, unless otherwise specified or clearly implied to the contrary by the context in which the reference is made.

All publications, articles, papers, patents, patent application publications, and other references cited herein are hereby incorporated in their entireties for all purposes to the extent consistent with the disclosure herein.

The term "$CB_2$" as described herein refers to the body's cannabinoid type 2 receptors.

The term "oily-prone skin" as described herein means skin having or at risk of having exaggerated secretion of sebum, such as a sebum concentration of greater than approximately 200 μg/cm$^2$ measured on the forehead.

The term "plant-based" as used herein is meant to encompass plant extracts. A "plant extract" refers to a composition produced by contacting a plant or a portion thereof with a solvent (e.g., water, oil, or organic solvent such as methanol, ethanol, acetonitrile, and the like), wherein one or more components of the plant are solubilized in the solvent. In some embodiments, "plant extract" also encompasses compositions derived from a plant's stem cells, such as in a bio-fermentation reactor, which may be referred to as being "nature identical." In further embodiments, "plant extract" comprises a dry composition, e.g., a powder, produced by crushing a plant or portion thereof.

After having diligently vetted combinations of plant-based ingredients, in varying amounts, the inventors surprisingly and unexpectedly stumbled upon a synergistic combination of certain plant-based active ingredients that, when formulated into a composition having a specific pH range and topically applied on the skin, facilitate regulation of sebum production in oily-prone skin, enable the proactive mitigation of skin disorders associated with oily-prone skin, and improve the appearance of acne-prone skin by reducing redness and diminishing the appearance of acne and acne-prone pores.

In some embodiments, the compositions provided herein are eligible for certification by ECOCERT®, COSMOS, and/or NOP. ECOCERT® is an organic certification organization based in Europe that conducts inspections in over 80 countries, making it one of the largest organic certification organizations in the world. COSMOS (Cosmetic Organic Standard) is a Europe-wide private standard to promote the use of ingredients from organic farming; use production and manufacturing processes that are environmentally sound and safe for human health; and include and expand the concept of "green chemicals." The National Organic Program (NOP) is a federal regulatory framework in the United States for developing and enforcing national standards for organically produced agricultural products.

Exaggerated sebum production is a known cause of acne formation as the sebum tends to solidify within the pores of the skin. The solidified sebum then plugs the pore, preventing newly secreted sebum from reaching the skin's surface, resulting in the formation of a pimple and its associated inflammation. The inflammation is caused by the chemokine IL-8 that acts in coordination with the proinflammatory cytokine TNF-α.

Cannabinoid type 2 receptors ($CB_2$) are transmembrane receptors, part of the human endocannabinoid system, that trigger protective intracellular pathways involved in anti-inflammatory and protective actions. They are markedly different from Cannabinoid type 1 receptors (CB') which play a role in facilitating psychotropic effects when activated by, for example, THC, the main psychoactive compound in marijuana.

The IL1-R1 gene is a mediator involved in numerous cytokine-induced immune and inflammatory responses. Activation of $CB_2$ causes a decrease in IL1-R1 gene activity and a concomitant decrease in cytokine-induced inflammation. Examples of plants whose extracts have the ability to activate $CB_2$ include *cannabis, Echinacea*, Rue, members of the plant genus *Brassica*, and Pogostemon Cablin leaf, also known as Patchouli.

The term $CB_2$ activator is intended to encompass those compounds capable of activating the body's $CB_2$ receptor. A particularly preferred $CB_2$ activator is a phytocannabinoid-infused Pogostemon Cablin extract, commercially available from Ashland Chemical of Wilmington, Del., USA, under the trade name $CB_2$-Skin™.

Marine algae capable of inhibiting the overproduction of sebum by the sebaceous glands may also be employed in order to address skin conditions caused by excess sebum production such as acne and seborrheic dermatitis. Sebaceous glands are stimulated by androgens such as testosterone. The enzyme 5-α-reductase converts testosterone in the skin into dihydrotestosterone (DHT), resulting in an overproduction of sebum. Excess sebum production is a known cause of acne formation as the sebum tends to solidify within the pores of one's skin. The solidified sebum then plugs the pore, preventing newly secreted sebum from reaching the skin's surface, resulting in the formation of a pimple and its associated inflammation. As described herein, the inflammation is caused by the chemokine IL-8 that acts in coordination with the proinflammatory cytokine TNF-α.

In some embodiments, the algal blend of *Tetraselmis chuii* and *Fucus spiralis* algae employed in the present invention reduces both excess sebum production and inflammation in the skin. Such a blend is commercially available from Gelyma, of Marseilles, France, under the trade name Sebocea®.

Gotukola (i.e., *Centella asiatica*) is believed in Ayurveda, i.e., ancient medical traditions practiced in India, Sri Lanka, and other South Asian countries, to be a cooling anti-inflammatory herb that helps fight chronic skin conditions such as eczema and psoriasis and may be capable of repairing damage done to the skin. It is also believed to promote alleviation of anxiety and to protect against oxidative stresses. *Centella asiatica* has also been used to treat inflammatory diseases in traditional Chinese medicine for thousands of years. The mechanisms of *Centella asiatica*'s inflammation-suppressing capabilities have been investigated. See, Cho et al., *The American Journal of Chinese*

*Medicine*, Vol. 48, No. 5, 1103-1120 (2020); Sukketsiri W, Tanasawet S, Moolsap F, Tantisira MEE, Hutamekalin P, Tipmanee V. "ECa 233 Suppresses LPS-Induced Proinflammatory Responses in Macrophages via Suppressing ERK1/2, p 38 MAPK and Akt Pathways," *Biol Pharm Bull*. 2019; 42(8):1358-1365. doi: 10.1248/bpb.b19-00248. PMID: 31366870; and Sun Boju, Wu Lili, Wu You, Zhang Chengfei, Qin Lingling, Hayashi Misa, Kudo Maya, Gao Ming, Liu Tonghua, "Therapeutic Potential of *Centella asiatica* and Its Triterpenes: A Review," *Frontiers in Pharmacology*, Vol. 11 (2020), p. 1373. For example, treatment with *Centella asiatica* may suppress nitric oxide production and iNOS expression in RAW 264.7 macrophages. *Centella asiatica* treatment may also reduce pro-inflammatory TNF-α and interleukin (IL)-6 levels.

In some embodiments, *Centella asiatica* is commercially sourced from Sederma S. A. in France, under the tradename Rubistem®.

Tulsi, also referred to as holy basil, is indigenous to the Indian continent and highly revered for its medicinal uses within the Ayurvedic and Siddha medical systems. Many in vitro, animal and human studies attest to Tulsi having multiple therapeutic actions. See, Jamshidi N, Cohen MM "The Clinical Efficacy and Safety of Tulsi in Humans: A Systematic Review of the Literature," *Evid Based Complement Alternat Med*. 2017:9217567. doi:10.1155/2017/9217567.

In some embodiments, Tulsi has anti-bacterial properties. In some embodiments, Tulsi is capable of boosting the skin's immune function, protecting it from environmental stress and the signs of aging. In some embodiments, Tulsi is an antiseptic that can clear bacteria from the skin and reduce acne and other forms of skin irritation.

According to one embodiment of the present disclosure, there is provided a topical composition for application onto oily-prone skin, the composition comprising: (1) a mixture of at least (a) from about 0.02 to about 1% by weight of an ingredient capable of activating a cannabinoid type-2 receptor; (b) from about 0.1 to about 3% by weight of a blend of *Tetraselmis chuii* and *Fucus spiralis* algae extracts; (c) from about 0.1 to about 4% by weight of an extract of *Centella asiatica*; and (d) from about 0.01 to about 0.05% by weight of an extract of Tulsi, all weights based on the total weight of the composition; (2) optionally, an emulsifier; and (3) a dermatologically acceptable carrier, wherein the composition has a pH ranging from about 4.5 to about 5.5, including from about 4.8 to about 5.3.

According to another embodiment of the present disclosure, there is provided a topical composition for application onto oily-prone skin, the composition comprising: (1) a mixture of at least (a) from about 0.02 to about 0.05% by weight of an ingredient capable of activating a cannabinoid type-2 receptor; (b) from about 0.5 to about 2.5% by weight of a blend of *Tetraselmis chuii* and *Fucus spiralis* algae extracts; (c) from about 1 to about 3% by weight of an extract of *Centella asiatica*; and (d) from about 0.01 to about 0.03% by weight of an extract of Tulsi, all weights based on the total weight of the composition; (2) optionally, an emulsifier; and (3) a dermatologically acceptable carrier, wherein the composition has a pH ranging from about 4.5 to about 5.5, including from about 4.8 to about 5.3.

In yet another embodiment of the present disclosure, there is provided a topical composition for application onto oily-prone skin, the composition comprising: (1) a mixture of at least (a) from about 0.02 to about 0.03% by weight of an ingredient capable of activating a cannabinoid type-2 receptor; (b) from about 1 to about 2% by weight of a blend of *Tetraselmis chuii* and *Fucus spiralis* algae extracts; (c) from about 1 to about 3% by weight of an extract of *Centella asiatica*; and (d) from about 0.01 to about 0.03% by weight of an extract of Tulsi, all weights based on the total weight of the composition; (2) optionally, an emulsifier; and (3) a dermatologically acceptable carrier, wherein the composition has a pH ranging from about 4.5 to about 5.5, including from about 4.8 to about 5.3.

According to another embodiment of the present disclosure, the inventors have surprisingly discovered that a natural preservative system comprising a combination of specific amounts of: a *Lactobacillus* ferment, a *Lactobacillus* and *Cocos nucifera* (coconut) fruit extract, salicylic acid (in some embodiments optional), potassium sorbate, and propanediol, in some embodiments petroleum-free 1,3-propanediol, when incorporated into a composition having a specific pH range, effectively both prohibits and inhibits microbial growth on and in the composition.

The *Lactobacillus* ferment of the present disclosure is preferably employed in an amount of from about 1 to about 5% by weight, preferably from about 2 to about 4% and more preferably from about 2 to about 4%, by weight of the total composition. A "*Lactobacillus* ferment" may refer to the solution obtained after fermentation of a defined growth medium by the bacterium *Lactobacillus* spp. During fermentation, *Lactobacillus* bacteria produce antimicrobial peptides that can provide broad spectrum antimicrobial protection at appropriate concentrations and/or in combination with other antimicrobial agents. An exemplary *Lactobacillus* ferment is commercially available from Active Micro Technologies under the tradename Leucidal® SF.

The *Lactobacillus* and *Cocos nucifera* fruit extract can include any *Cocos nucifera* fruit extract fermented with *Lactobacillus* and/or included with *Lactobacillus* ferment of the present disclosure and is preferably employed in an amount of from about 1 to about 5%, preferably from about 2 to about 4%, by weight of the total composition. "*Cocos nucifera* fruit extract fermented with *Lactobacillus*" may reference the solution obtained after *Lactobacillus* fermentation of *Cocos nucifera* (coconut) fruit extract instead of a defined growth medium. The result is a materially different antimicrobial product that is effective at preventing the growth of fungi, specifically yeasts and molds, at appropriate concentrations and/or in combination with other antimicrobial agents. An exemplary *Lactobacillus* and *Cocos nucifera* extract is commercially available from Active Micro Technologies under the tradename Amticide® Coconut and is typically associated with the International Nomenclature of Cosmetic Ingredients (INCI) name of a *Lactobacillus* and *Cocos nucifera* (coconut) fruit extract.

When present, salicylic acid is preferably employed in an amount of up to about 0.5% by weight, preferably from about 0.1 to about 0.45%, and more preferably from about 0.2 to about 0.4%, by weight of the total composition. It should be noted that the use of salicylic acid in an amount at or greater than about 0.5% by weight, based on the total weight of the composition, renders the composition a drug requiring FDA approval prior to commercialization and sale in the United States. In some embodiments, salicylic acid may be omitted by adjusting the concentrations of *Lactobacillus* ferment, *Lactobacillus* and *Cocos nucifera* fruit extract, and/or other ingredients as described in greater detail herein.

When present, the salt of a weak acid is employed in an amount of up to about 0.5% by weight, preferably from about 0.1 to about 0.45% and more preferably from about 0.2% to about 0.4%, by weight of the total composition. A preferred salt of a weak acid is potassium sorbate (i.e., the potassium salt of sorbic acid). Other weak acids that may be used in their salt form include, but are not limited to, acetic acid, propionic acid, and benzoic acid, such as sodium benzoate.

Propanediol, such as a petroleum-free 1, 3-propanediol is typically employed in an amount of from about 1% to about 10% by weight, preferably from about 2% to about 8% and more preferably from about 4% to about 6%, by weight of the total composition. An exemplary petroleum-free 1,3-propanediol is commercially available from Dupont Tate & Lyle Bio Products under the tradename Zemea® Propanediol and can be associated with the INCI name propanediol.

The inventors have unexpectedly discovered that the ability of the preservative system of the present disclosure to effectively inhibit microorganism growth is critically dependent on the pH of the composition in which it is used. For example, if the preservative system is employed in a composition having a pH of 6, it fails to provide the requisite broad-spectrum protection needed for acceptable storage stability/shelf-life. Accordingly, the pH of a composition comprising the preservative system of the present disclosure must be in a range of from about 4.5 to about 5.5, and preferably from about 4.8 to about 5.3.

In this embodiment of the present disclosure, there is provided a composition intended for application onto human skin in order to enhance its health and appearance, the composition comprising: (1) a mixture of at least: (a) from about 0.02 to about 1% by weight, preferably from about 0.02 to about 0.05 by weight, and more preferably from about 0.02 to about 0.03% by weight of an ingredient capable of a activating cannabinoid type-2 receptor; (b) from about 0.1 to about 3.0% by weight, preferably from about 0.5 to about 2.5% by weight, and more preferably from about 1 to about 2% by weight of a blend of *Tetraselmis chuii* and *Fucus spiralis* algae extracts; (c) from about 0.1 to about 4% by weight, preferably from about 1 to about 3% by weight, and more preferably from about 1.5 to about 2.5% by weight of *Centella asiatica* extract; and (d) from about 0.01 to about 0.05% by weight, preferably from about 0.01 to about 0.03% by weight, and more preferably from about 0.02 to about 0.03% by weight of Tulsi extract; (2) optionally, an emulsifier; (3) a preservative system that includes: (A) from about 1 to about 5%, preferably from about 2 to about 4% by weight, of a *Lactobacillus* ferment; (B) from about 1 to about 5%, preferably from about 2 to about 4% by weight, of *Lactobacillus* and *Cocos nucifera* fruit extract; (C) up to about 0.5% by weight, preferably from about 0.1 to about 0.45% by weight, and more preferably from about 0.25 to about 0.4% by weight, of salicylic acid; (D) up to about 0.5% by weight, preferably from about 0.2 to about 0.4% by weight, of at least one salt of a weak acid, preferably potassium sorbate; and (E) from about 1 to about 10%, preferably from about 2 to about 8% by weight, and more preferably from about 4 to about 6% by weight of propanediol, all weights based on the total weight of the composition; and (4) a dermatologically acceptable carrier, wherein the composition has a pH ranging from about 4.5 to about 5.5, and preferably from about 4.8 to about 5.3.

The dermatologically acceptable carrier can encompass a wide variety of forms. In some cases, the solubility or dispersibility of the components in the composition may dictate the form and character of the carrier. Non-limiting examples include simple solutions (e.g., aqueous, or anhydrous), dispersions, emulsions, and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water). While the oil phase may comprise any vegetable oil, so long as it does not cause skin sensitization, a particularly preferred oil component is almond oil.

The inventors have surprisingly discovered that the use of almond oil enables bioactive compounds present in the plant-based extract to more effectively penetrate the epidermis, without the need of having to use skin-sensitizing essential oils, while still facilitating the desired degree of efficacy. This is due to almond oil being rich in beta-zoosterol, squalene, and alpha-tocopherol, together with lesser amounts of carbohydrates, proteins, and vitamins and minerals such as vitamin B complex (comprising at least one of vitamins B1, B2, B3, B5, B6, B7, B9, and B12) and zinc. Moreover, almond oil's phytochemicals are believed to be effective at promoting surface level proliferation and skin cell development. Other vegetable oils that may also be used include, but are not limited to, olive oil, jojoba oil, babassu oil, castor oil, coconut oil, mango oil, moringa oil, neem oil, corn oil, cotton seed oil, linseed oil, mustard oil, safflower oil, sesame oil, soybean oil, sunflower-seed oil, wheat germ oil, argan oil, and marula oil.

In the event the use of an emulsifier is necessary, any ingredient capable of emulsifying the composition may be employed without departing from the spirit of the disclosure, so long as it is natural and/or dermatologically acceptable. Examples thereof include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

The compositions of the present disclosure may be made available to consumers in a wide variety of product forms that include, but are not limited to, solutions, suspensions, lotions, creams, gels, sprays, ointments, foams, and serums. For example, a product intended for application onto skin, post-shaving, to help relieve the irritation associated with the mechanical stress on the skin caused by the shaving process, can be formulated using the above-described compositions as a base formula.

As an additional example, the composition may be available as a mist/toner for sebum control. It may have antibacterial properties that can be beneficial for use throughout many (if not all) times of day. As an additional example, compositions of the present disclosure may be in the form of a serum to alleviate skin irritation caused by inflammation and may help to prevent touching/scratching of the irritated skin, which would tend to make the irritation worse.

According to embodiments of the present disclosure, the compositions can also additionally comprise suitable auxiliary ingredients as desired. For example, the composition can include other active or inactive ingredients, provided they do not unacceptably alter the benefits of the skin care composition, are natural, and/or do not promote skin sensitization.

Examples of auxiliary ingredients that may be employed in order to further potentiate the invention's efficacy include, but are not limited to, humectants, emollients, flavonoids, minerals, chelating agents, pH regulators/buffers, rheology modifiers, phytosterols, vitamin $B_3$ compound, *Betula alba* extract, glycolipids, plant-based meroterpenes such as Bakuchiol, salicylic acid, benzoyl peroxide, sulfur, fruit acids, gluconolactone, antimicrobial peptides, preferably Oligopeptide-10 available from Grant Industries of Elmwood Park, N.J., USA, anti-inflammatory agents such as licorice extracts, bisabolol, guggal extracted from plants in the genus *Commiphora*, *Quillaja saponaria* extract, kola extract, chamomile extract, red clover extract, sea whip extract, hibiscus extract, lucuma extract, sea kale extract, *Cetraria islandica* L. (Iceland moss) extract, *Amelanchier alnifolia* (Saskatoon berry) extract, *Acanthopanax senticosus* (Siberian ginseng) extract, *Picea abies* (Spruce needles) extract, *Betula alba* (birch bark) extract, *Vaccinium myrtillus* (blueberry) extract, *Vaccinium macrocarpon* (cranberry) extract yarrow extract, marigold extract, couch grass extract, *Nigella sativa* extract, Dragons Blood, extract, *Brahmi* extract, *Asparagus rocemosus* extract, prickly pear, *Opuntia* oil, jojoba, lavender extract, rosemary oil, *Arnica* extract, *Chamomille* extract *Valerian root* extract, Clove extract, argan oil, *Astrocaryum murumuru* seed butter, *Theobroma grandiflorum* seed butter, *Theobroma grandiflorum* seed butter, *Spondias mombin* pulp extract, *Mangifera indica* pulp extract, *Musa sapientum* pulp extract, *Mauritia flexuosa* fruit oil, *Physalis angulata* extract, *Xylityl sesquicaprylate*, *Vaccinium myrtillus* seed oil, *Cucubita pepo* seed extract, linoleic acid, linolenic acid, *Tamarindus indica* see polysaccharide, *Zanthoxylum bungeanum* fruit extract, *Lactococcus* ferment lysate, *Bellis perennis* flower extract, *Coffea arabica* seed cake extract, *Coffea arabica* seed oil, cotton seed oil, linseed oil, *Pichia* ferment lysate filtrate, chlorophyll, cardamom, lotus flower extract, clove oil, nutmeg, marigold, and whey protein.

In some embodiments, the composition comprises one or more auxiliary active ingredients that ameliorates, treats, or prevents acne. Acne is a multifactorial disease. Increased sebum production by androgen stimulation, abnormal hyperkeratinization of the pilosebaceous duct, and subsequent bacterial colonization and inflammation all contribute to the disease. It has been proposed that *P. acnes* colonization plays a pivotal role in the pathogenesis of acne since antimicrobial therapy has been effective in treating acne for many years.

*Propionibacterium acnes* is a Gram-positive, anaerobic/microaerophilic, fat-splitting, rod-shaped bacterium found on the skin. It represents approximately 90% of the skin microbiome of healthy adults. The concentration of *P. acnes* depends on the abundance of sebaceous follicles and the age of an individual. Accordingly, its concentration is higher on sebaceous areas such as the face, scalp, and back and studies have shown an association between *P. acnes* levels and sebum production. *P. acnes* may disrupt keratinocyte differentiation in the follicle, thereby contributing to the formation of comedones and inflammatory acne lesions by triggering a host inflammatory response. *P. acnes* produces enzymes that degrade skin components as well as chemotactic factors that stimulate keratinocytes and inflammatory cells to release pro-inflammatory cytokines and reactive oxygen species.

Antibiotic resistance is among the main causes of treatment failure in acne vulgaris caused, primarily, by gene mutation. Long-term use of antibiotics can promote the formation of an antibiotic-resistant biofilm that protects the bacterium against host defenses and can alter the natural microbiota of the skin. The dominant bacterial species found on adult skin are *Propionibacterium*, *Corynebacterium*, and *Staphylococcus*.

Bacteriophages, i.e., viruses that infect bacteria, are essential members of the human microbiome and, as a result, may play an important regulatory role in human skin health and disease. There are over 6,000 well-known bacteriophages having a broad diversity in structure (tailed, polyhedral, pleomorphic and filamentous) that are typically classified based on their genetic makeup. They have four distinct life cycle phases: lytic, lysogenic, pseudo-lysogenic and chronic infection. The first step in every phage cycle is the binding of the phage to bacterial surface receptors, after which the phage injects its genetic material (DNA or RNA) into the cells. Phages undergoing the lytic phase are the most abundant and widely used in bacteriophage therapy due to their natural ability to kill bacteria directly through cell lysis. In the lysogenic phase, phage have the ability to induce transduction which can facilitate genetically engineered phages to transfer genes to reverse antibiotic resistance or to increase bacterial susceptibility to antibiotics, thereby enhancing the killing of antibiotic-resistant bacteria and biofilm.

*P. acnes* bacteriophage genomes encode endolysins involved in bacteria cell-wall degradation. Phage endolysins have been used as antimicrobials both in vitro and in vivo with promising results, without any resistance to said phage endolysins having been observed. As a result, it has also been theorized that genetically engineered enzymes can be used to target bacteria cell walls in order to treat acne.

In view of the above, additional auxiliary ingredients that may also be employed in the compositions and method of the present disclosure include biotech-manufactured phages such as macrophages or bacteriophages that have been intentionally genetically engineered to target *C. acnes* (a.k.a., *P. acnes*) or *S. epidermis*. Especially preferred bacteriophages are those undergoing lytic cycles capable of rapidly killing their *P. acnes* host. Additionally, genetically engineered enzymes made to target and destroy the cell walls of *P. acnes* can also be used in the invention of the present disclosure. Without intending to be bound by theory, it is believed by the inventors that use of such genetically engineered phages and/or enzymes in the compositions of the present invention can more rapidly diminish the appearance and/or formation of acne by managing acne-causing sebum production while simultaneously killing acne-causing *P. acnes* bacteria.

Each optional/auxiliary ingredient may be employed in a range of from about 0.1 to about 10% by weight, including all ranges therebetween such as from about 0.1 to about 5.0% by weight, and from about 0.5 to about 4.0% by weight, and from about 1.0 to about 3.0% by weight, and from about 1.5 to about 2.5% by weight, all weights based on the total weight of the composition.

When formulating an OTC acne treatment product capable of more rapidly diminishing the appearance of acne, a particularly useful auxiliary ingredient for use in the present composition is sulfur, an FDA approved anti-acne active ingredient. When present, sulfur can be employed in an amount of from about 2 to about 10% by weight, preferably from about 4 to about 7% by weight, and more preferably from about 5 to about 6% by weight, all weights based on the total weight of the composition. While sulfur is a preferred anti-acne active ingredient for use in the present invention, any other anti-acne active ingredient permitted for use in a particular country pursuant to that country's regulatory guidelines may also be used such as salicylic acid, benzoyl peroxide per FDA guidelines.

Without intending to be bound by theory, it is believed by the inventors that compositions in accordance with the present disclosure, when combined with an anti-acne active ingredient such as sulfur, for example, facilitate a synergistic decrease in the appearance of acne due to the combinatorial effects of sebum regulation, inflammation reduction, and *P. acnes* bacteria elimination. Additional anti-acne active ingredients that may also be used include benzoyl peroxide, salicylic acid, retinoids, and the like. The precise amount to be used depends on the formulary regulations of the geographical location in which these types of products are sold, such as the FDA for products sold in the US.

In yet another embodiment of the present disclosure, there is provided a composition intended for application onto oily-prone skin, the composition containing: (1) a mixture of at least: (a) from about 0.02 to about 1.0% by weight, including from about 0.02 to about 0.05% by weight, and from about 0.02 to about 0.03% by weight of an ingredient capable of activating a cannabinoid type-2 receptor, preferably a phytocannabinoid-infused Pogostemon Cablin leaf extract; (b) from about 0.1 to about 3.0% by weight, including from about 0.5 to about 2.5% by weight, and from about 1.0 to about 2.0% of a blend of *Tetraselmis chuii* and *Fucus spiralis* algae extracts; (c) from about 0.1 to about 4.0% by weight, including from about 1.0 to about 3.0% by weight, and from about 1.5 to about 2.5% by weight of *Centella asiatica* plant extract; (d) from about 0.01 to about 0.05% by weight, including from about 0.01 to about 0.03% by weight of an extract of Tulsi; and (e) from about 0.1 to about 10% by weight, including from about 0.1 to about 4.0% by weight, and from about 0.5 to about 5.0% by weight, and from about 1.0 to about 3.0% by weight, and from about 1.5 to about 2.5% by weight, of at least one auxiliary active ingredient selected from *Betula alba* extract, a glycolipid, a plant-based meroterpene, preferably Bakuchiol, an anti-acne active ingredient, preferably sulfur, fruit acids, gluconolactone, an antimicrobial peptide, preferably Oligopeptide-10, and a genetically-engineered bacteriophage targeted for killing *P. acnes* and/or *S. epidermis* bacteria and/or a genetically-engineered *P. acnes* biofilm degrading enzyme; (2) an emulsifier; and (3) a dermatologically-acceptable carrier. In embodiments, the composition has a pH of about 4.5 to about 5.5, for example, about 4.8 to about 5.3.

In yet another embodiment of the present disclosure, there is provided a method of managing exaggerated sebum production in oily-prone skin to proactively inhibit the occurrence of disorders associated with oily-prone skin, improve the appearance of acne-prone skin, and diminish the appearance of acne, by topically applying one of the above-disclosed compositions onto skin.

In some embodiments, the present disclosure provides a method of managing exaggerated sebum production in oily-prone skin, the method comprising applying onto the skin a composition that comprises: (1) a mixture of at least: (a) from about 0.02 to about 1% by weight of an ingredient capable of activating cannabinoid type-2 receptors; (b) from about 0.1 to about 3% by weight of a blend of *Tetraselmis chuii* and *Fucus spiralis* algae extracts; (c) from about 0.1 to about 4% by weight of an extract of *Centella asiatica*; and (d) from about 0.01 to about 0.05% by weight of an extract of Tulsi, wherein all weights are based on the total weight of the composition; (2) optionally, an emulsifier; and (3) a dermatologically acceptable carrier, wherein the composition has a pH ranging from about 4.5 to about 5.5.

In further embodiments, the disclosure provides a method of managing exaggerated sebum production in oily-prone skin, the method comprising applying onto the skin a composition that comprises: (1) a mixture of at least: (a) from about 0.02 to about 0.03% by weight of a phytocannabinoid-infused Pogostemon Cablin extract; (b) from about 1 to about 2% by weight of a blend of *Tetraselmis chuii* and *Fucus spiralis* algae extracts; (c) from about 1.5 to about 2.5% by weight of *Centella asiatica* extract; and (d) from about 0.02 to about 0.03% by weight of Tulsi extract; (2) optionally, an emulsifier; (3) a preservative system containing: (A) from about 2 to about 4% by weight, of a *Lactobacillus* ferment; (B) from about 2 to about 4% by weight, of *Lactobacillus* and *Cocos nucifera* fruit extract; (C) from about 0.25 to about 0.4% by weight, of salicylic acid; (D) from about 0.2 to about 0.4% by weight of potassium sorbate; and (E) from about 4 to about 6% by weight of propanediol, wherein all weights are based on total weight of the composition; (4) a dermatologically acceptable carrier; and (5) optionally, at least one auxiliary ingredient chosen from an anti-acne active ingredient, an antimicrobial peptide, a bacteriophage targeted for *C. acnes*, a bacteriophage targeted for *S. epidermis*, and a combination thereof, wherein the composition has a pH ranging from about 4.5 to about 5.5.

EXAMPLES

The following examples as set forth herein are intended for illustrative purposes only and are not intended to limit the scope of the invention in any way, as many variations thereof are possible without departing from the spirit and scope of the invention. In the examples, all concentrations are listed as weight percent, unless otherwise specified.

Example 1

A balancing foaming cleanser composition in accordance with the present invention may be made per the following formulation.

| Ingredient | Weight percent |
| --- | --- |
| *Centella asiatica* | 1.00 |
| Blend of *Tetraselmis chuii* and *Fucus spiralis* algae extracts | 1.00 |
| Phytocannabinoid-infused *Pogostemon Cablin* leaf extract | 0.02 |
| Tulsi | 0.02 |
| Propanediol | 4.00 |
| *Lactobacillus* ferment | 4.00 |
| *Lactobacillus* and *Cocos nucifera* fruit extract | 2.00 |
| Sodium benzoate | 0.30 |
| Potassium sorbate | 0.20 |
| Citric acid | 0.20 |
| water | 72.51 |
| auxiliaries | 14.75 |
| Total | 100.00 |

The composition of Example 1 was clinically tested to evaluate its ability to inhibit sebum production, influence acne formation, and improve the appearance of acne-prone skin over a period of twenty-eight days. Twenty-seven individuals aged 18-30 having naturally greasy skin (39% of individuals) and combination skin (61% of individuals) were asked to apply the composition twice a day at home, once in the morning and once in the evening, under normal use conditions, as a replacement for their normal skin care routine.

Comedogenic potential was evaluated based on the number of blackheads, microcysts, papules and pustules (i.e., "elements") detected on the face at the beginning and end of the study to ascertain whether use of the composition could influence comedone and acne formation. On day 0 and day 28 a dermatologist counted the number of elements on each volunteer's entire face, except for the nasal pyramid, the vermillion border, the crease of the chin and the rim of the scalp. The results showed that there was no statistically significant increase in the number of elements after 28 days of use, thereby evidencing the ability of the composition to positively influence an individual's comedogenic/acneigenic potential.

Next, the composition was evaluated to ascertain its ability to influence sebum production. To do so, the quantity of sebum present on the face of each individual was measured on day 0 and day 28 using a Sebumeter® SM 815 commercially available from Courage & Khazaka. The results showed that after 28 days approximately 64% of the test subject experienced a 13% decrease in cutaneous sebum rate evidencing the sebum-regulating effect of the composition.

The ability of the composition to induce an anti-redness effect on the skin was also evaluated using a C-Cube 2® commercially available from Pixience on day 0 and day 28. The results showed that >60% of the test subjects experienced a 5% decrease in skin redness (considered "significant") on their face, evidencing the ability of the composition to improve the appearance of oily, acne-prone skin and positively influence acne formation via a reduction in skin inflammation.

Lastly, the composition was also evaluated to determine its ability to influence acne formation on oily-prone skin by measuring corneocyte adhesion. Skin samples were removed from the cheekbone of volunteers using D-Squam® strips on day 0 and day 28. The samples were then analyzed using a Skin Image Analyzer® with QuantiSquam® software by studying a 1 cm$^2$ area of skin sample using a digital camera connected to a computer. The results showed that 83% of the test subjects experienced a significant decrease (>50%) in skin desquamation, evidencing improved corneocyte cohesion. Since acne-prone skin is known to shed more follicle-clogging dead skin cells than average, an improvement in corneocyte cohesion means that there is less of a likelihood that dead skin cells will accumulate at the base of a hair follicle, cause a blockage, and create an environment where bacteria can buildup and trigger acne formation.

Example 2

A balancing toner composition in accordance with the present invention may be made per the following formulation.

| Ingredient | Weight percent |
| --- | --- |
| Centella asiatica | 2.00 |
| Blend of Tetraselmis chuii and Fucus spiralis algae extracts | 1.00 |
| Phytocannabinoid-infused Pogostemon Cablin leaf extract | 0.02 |
| Tulsi | 0.02 |
| Propanediol | 4.00 |
| Lactobacillus ferment | 4.00 |
| Lactobacillus and Cocos nucifera fruit extract | 2.00 |
| Sodium benzoate | 0.30 |
| Potassium sorbate | 0.20 |
| Citric acid | 0.10 |
| water | 70.26 |
| auxiliaries | 16.10 |
| Total | 100.00 |

The composition of Example 2 was clinically tested to evaluate its ability to influence acne formation and improve the appearance of acne-prone skin over a period of twenty-eight days. Twenty-nine individuals aged 18-40 having naturally greasy skin (31% of individuals) and combination skin (69% of individuals) were asked to apply the composition twice a day at home, once in the morning and once in the evening, under normal use conditions, as a replacement for their normal skin care routine.

Comedogenic potential was evaluated based on the number of blackheads, microcysts, papules and pustules (i.e., "elements") detected on the face at the beginning and end of the study to ascertain whether use of the composition could influence comedone and acne formation. On day 0 and day 28 a dermatologist counted the number of elements on each volunteer's entire face, except for the nasal pyramid, the vermillion border, the crease of the chin and the rim of the scalp. The results showed that there was no statistically significant increase in the number of elements after 28 days of use, thereby evidencing the ability of the composition to positively influence an individual's comedogenic/acneigenic potential.

The ability of the composition to induce an anti-redness effect on the skin was also evaluated using a C-Cube 2® commercially available from Pixience on day 0 and day 28. The results showed that >75% of the test subjects experienced a 6% decrease in skin redness (considered "significant") on their face, evidencing the ability of the composition to improve the appearance of oily, acne-prone skin and positively influence acne formation via a reduction in skin inflammation.

Lastly, the composition was also evaluated to determine its ability to influence acne formation on oily-prone skin by measuring corneocyte adhesion. Skin samples were removed from the cheekbone of volunteers using D-Squam® strips on day 0 and day 28. The samples were then analyzed using a Skin Image Analyzer® with QuantiSquam® software by studying a 1 cm$^2$ area of skin sample using a digital camera connected to a computer. The results showed that 71% of the test subjects experienced a significant decrease (>30%) in skin desquamation, evidencing improved corneocyte cohesion. Since acne-prone skin is known to shed more follicle-clogging dead skin cells than average, an improvement in corneocyte cohesion means that there is less of a likelihood that dead skin cells will accumulate at the base of a hair follicle, cause a blockage, and create an environment where bacteria can buildup and trigger acne formation.

Example 3

A balancing/purifying mask composition in accordance with the present invention may be made per the following formulation.

| Ingredient | Weight percent |
| --- | --- |
| Centella asiatica | 0.01 |
| Blend of Tetraselmis chuii and Fucus spiralis algae extracts | 0.10 |
| Phytocannabinoid-infused Pogostemon Cablin leaf extract | 0.02 |
| Tulsi | 0.02 |
| Turmeric | 0.10 |
| Lactobacillus ferment | 4.00 |
| Lactobacillus and Cocos nucifera fruit extract | 2.00 |
| Sodium benzoate | 0.30 |
| Potassium sorbate | 0.20 |
| Citric acid | 0.25 |
| water | 63.56 |
| auxiliaries | 29.44 |
| Total | 100.00 |

The composition of Example 3 was clinically tested to evaluate its ability to inhibit sebum production, influence acne formation, and improve the appearance of acne-prone skin over a period of twenty-eight days. Twenty-nine individuals aged 18-39 having naturally greasy skin (24% of individuals) and combination skin (76% of individuals) were asked to apply the composition twice a day at home, once in the morning and once in the evening, under normal use conditions, as a replacement for their normal skin care routine.

First, the composition was evaluated to ascertain its ability to influence sebum production. To do so, the Next, the quantity of sebum present on the face of each individual was measured on day 0 and day 28 using a Sebumeter® SM 815 commercially available from Courage & Khazaka. The results showed that after 28 days approximately 64% of the test subject experienced a 14% decrease in cutaneous sebum rate evidencing the sebum-regulating effect of the composition.

The ability of the composition to induce an anti-redness effect on the skin was also evaluated using a C-Cube 2® commercially available from Pixience on day 0 and day 28. The results showed that >80% of the test subjects experienced a 7% decrease in skin redness (considered "significant") on their face, evidencing the ability of the composition to improve the appearance of oily, acne-prone skin and positively influence acne formation via a reduction in skin inflammation.

Lastly, the composition was also evaluated to determine its ability to influence acne formation on oily-prone skin by measuring corneocyte adhesion. Skin samples were removed from the cheekbone of volunteers using D-Squam® strips on day 0 and day 28. The samples were then analyzed using a Skin Image Analyzer® with QuantiSquam® software by studying a 1 cm² area of skin sample using a digital camera connected to a computer. The results showed that >80% of the test subjects experienced a significant decrease (>65%) in skin desquamation, evidencing improved corneocyte cohesion. Since acne-prone skin is known to shed more follicle-clogging dead skin cells than average, an improvement in corneocyte cohesion means that there is less of a likelihood that dead skin cells will accumulate at the base of a hair follicle, cause a blockage, and create an environment where bacteria can buildup and trigger acne formation.

Example 4

A balancing cream treatment composition in accordance with the present invention may be made per the following formulation.

| Ingredient | Weight percent |
| --- | --- |
| *Centella asiatica* | 1.00 |
| Blend of *Tetraselmis chuii* and *Fucus spiralis* algae extracts | 1.00 |
| Phytocannabinoid-infused *Pogostemon Cablin* leaf extract | 0.02 |
| *Tulsi* | 0.02 |
| Propanediol | 4.00 |
| *Lactobacillus* ferment | 4.00 |
| *Lactobacillus* and *Cocos nucifera* fruit extract | 2.00 |
| Sodium benzoate | 0.30 |
| Potassium sorbate | 0.20 |
| Citric acid | 0.20 |
| water | 59.81 |
| auxiliaries | 27.45 |
| Total | 100.00 |

The composition of Example 4 was clinically tested to evaluate its ability to inhibit sebum production, influence acne formation, and improve the appearance of acne-prone skin over a period of twenty-eight days. Twenty-seven individuals aged 18-30 having naturally greasy skin (26% of individuals) and combination skin (74% of individuals) were asked to apply the composition twice a day at home, once in the morning and once in the evening, under normal use conditions, as a replacement for their normal skin care routine.

Comedogenic potential was evaluated based on the number of blackheads, microcysts, papules and pustules (i.e., "elements") detected on the face at the beginning and end of the study to ascertain whether use of the composition could influence comedone and acne formation. On day 0 and day 28 a dermatologist counted the number of elements on each volunteer's entire face, except for the nasal pyramid, the vermillion border, the crease of the chin and the rim of the scalp. The results showed that there was no statistically significant increase in the number of elements after 28 days of use, thereby evidencing the ability of the composition to positively influence an individual's comedogenic/acneigenic potential.

Next, the composition was evaluated to ascertain its ability to influence sebum production. To do so, the quantity of sebum present on the face of each individual was measured on day 0 and day 28 using a Sebumeter® SM 815 commercially available from Courage & Khazaka. The results showed that after 28 days approximately 64% of the test subject experienced a 13% decrease in cutaneous sebum rate evidencing the sebum-regulating effect of the composition.

The ability of the composition to induce an anti-redness effect on the skin was also evaluated using a C-Cube 2® commercially available from Pixience on day 0 and day 28. The results showed that >60% of the test subjects experienced a 5% decrease in skin redness (considered "significant") on their face, evidencing the ability of the composition to improve the appearance of oily, acne-prone skin and positively influence acne formation via a reduction in skin inflammation.

Lastly, the composition was also evaluated to determine its ability to influence acne formation on oily-prone skin by measuring corneocyte adhesion. Skin samples were removed from the cheekbone of volunteers using D-Squam® strips on day 0 and day 28. The samples were then analyzed using a Skin Image Analyzer® with QuantiSquam® software by studying a 1 cm² area of skin sample using a digital camera connected to a computer. The results showed that 83% of the test subjects experienced a significant decrease (>50%) in skin desquamation, evidencing improved corneocyte cohesion. Since acne-prone skin is known to shed more follicle-clogging dead skin cells than average, an improvement in corneocyte cohesion means that there is less of a likelihood that dead skin cells will accumulate at the base of a hair follicle, cause a blockage, and create an environment where bacteria can buildup and trigger acne formation.

What is claimed is:

1. A composition intended for application onto oily-prone skin, the composition comprising:
    (1) a mixture of at least:
        (a) about 0.02 to about 1% by weight of an extract capable of activating a cannabinoid type-2 receptor selected from *Cannabis, Echinacea*, Rue, members of the plant genus *Brassica*, and a Pogostemon Cablin leaf;

(b) about 0.1 to about 3% by weight of a blend of *Tetraselmis chuii* and *Fucus spiralis* algae extracts; and
(c) about 0.1 to about 4% by weight of an extract of *Centella asiatica*;
wherein all weights are based on total weight of the composition;
(2) optionally, an emulsifier; and
(3) a dermatologically acceptable carrier,
wherein the composition has a pH ranging from about 4.5 to about 5.5.

2. The composition of claim 1, wherein (a) is employed in an amount of from about 0.02 to about 0.05% by weight, based on the total weight of the composition.

3. The composition of claim 1, wherein (a) is employed in an amount of from about 0.02 to about 0.03% by weight, based on the total weight of the composition.

4. The composition of claim 1, wherein (b) is employed in an amount of from about 0.5 to about 2.5% by weight, based on the total weight of the composition.

5. The composition of claim 1, wherein (b) is employed in an amount of from about 1.0 to about 2.0% by weight, based on the total weight of the composition.

6. The composition of claim 1, wherein (c) is employed in an amount of from about 1.0 to about 3.0% by weight, based on the total weight of the composition.

7. The composition of claim 1, wherein (c) is employed in an amount of from about 1.5 to about 2.5% by weight, based on the total weight of the composition.

8. The composition of claim 1, further comprising from about 0.1 to about 10% by weight, based on the total weight of the composition, of at least one auxiliary active ingredient selected from *Betula alba* extract, a glycolipid, Bakuchiol, an anti-acne active ingredient, an antimicrobial peptide, a bacteriophage, a genetically engineered enzyme capable of degrading *P. acnes* biofilm, and combinations thereof.

9. The composition of claim 8, wherein the at least one auxiliary active ingredient is selected from: an anti-acne active ingredient, a genetically engineered bacteriophage targeted for *P. acnes*, a genetically engineered bacteriophage targeted for *S. epidermis*, and combinations thereof.

10. The composition of claim 1, wherein (a) comprises a phytocannabinoid-infused Pogostemon Cablin extract.

11. The composition of claim 1, further comprising a preservative system that comprises:
(A) from about 1 to about 5% by weight, of a *Lactobacillus* ferment;
(B) from about 1 to about 5% by weight, of *Lactobacillus* and *Cocos nucifera* fruit extract;
(C) up to about 0.5% by weight of salicylic acid;
(D) up to about 0.5% by weight of at least one salt of a weak acid; and
(E) from about 1 to about 10% by weight of propanediol, all weights based on the total weight of the composition.

12. The composition of claim 1, further comprising from about 0.01 to about 0.05% by weight of an extract of Tulsi.

13. The composition of claim 9, wherein the anti-acne active ingredient is selected from salicylic acid, sulfur, a fruit acid, gluconolactone, and combination thereof.

14. The composition of claim 1, wherein (a) is employed in an amount of from about 0.02 to about 0.05% by weight, (b) is employed in an amount of from about 0.5 to about 2.5% by weight, and (c) is employed in an amount of from about 1.0 to about 3.0% by weight.

15. A composition intended for application onto human skin in order to enhance its health and appearance, the composition comprising:
(1) a mixture of at least:
(a) from about 0.02 to about 0.03% by weight of a phytocannabinoid-infused Pogostemon Cablin extract;
(b) from about 1 to about 2% by weight of a blend of *Tetraselmis chuii* and *Fucus spiralis* algae extracts;
(c) from about 1.5 to about 2.5% by weight of *Centella asiatica* extract; and
(d) from about 0.02 to about 0.03% by weight of Tulsi extract;
(2) optionally, an emulsifier;
(3) a preservative system comprising:
(A) from about 2 to about 4% by weight, of a *Lactobacillus* ferment;
(B) from about 2 to about 4% by weight, of *Lactobacillus* and *Cocos nucifera* fruit extract;
(C) from about 0.25 to about 0.4% by weight, of salicylic acid;
(D) from about 0.2 to about 0.4% by weight of potassium sorbate; and
(E) from about 4 to about 6% by weight of propanediol,
wherein all weights are based on total weight of the composition;
(4) a dermatologically acceptable carrier; and
(5) optionally, at least one auxiliary ingredient selected from *Betula alba* extract, a glycolipid, Bakuchiol, an anti-acne active ingredient, an antimicrobial peptide, a bacteriophage, a genetically engineered enzyme capable of degrading *P. acnes* biofilm, and combinations thereof,
wherein the composition has a pH ranging from about 4.8 to about 5.3.

16. The composition of claim 15, wherein the auxiliary ingredient is selected from: an anti-acne active ingredient, a genetically engineered bacteriophage targeted for *P. acnes*, a genetically engineered bacteriophage targeted for *S. epidermis*, and combinations thereof; optionally wherein the anti-acne ingredient is selected from salicylic acid, sulfur, a fruit acid, a gluconolactone, and combinations thereof.

17. A method of managing exaggerated sebum production in oily-prone skin, the method comprising applying onto the skin a composition that comprises:
(1) a mixture of at least:
(a) about 0.02 to about 1% by weight of an extract capable of activating a cannabinoid type-2 receptor selected from *Cannabis, Echinacea*, Rue, members of the plant genus *Brassica*, and a Pogostemon Cablin leaf;
(b) about 0.1 to about 3% by weight of a blend of *Tetraselmis chuii* and *Fucus spiralis* algae extracts; and
(c) about 0.1 to about 4% by weight of an extract of *Centella asiatica*;
wherein all weights are based on the total weight of the composition;
(2) optionally, an emulsifier; and
(3) a dermatologically acceptable carrier,
wherein the composition has a pH ranging from about 4.5 to about 5.5.

18. The method of claim 17, wherein (a) is employed in an amount of from about 0.02 to about 0.03% by weight, based on the total weight of the composition.

19. The method of claim 17, wherein (b) is employed in an amount of from about 1.0 to about 2.0% by weight, based on the total weight of the composition.

20. The method of claim 17, wherein (c) is employed in an amount of from about 1.0 to about 3.0% by weight, based on the total weight of the composition.

21. The method of claim 17, wherein the composition further comprises from about 0.1 to about 10% by weight, based on the total weight of the composition, of at least one auxiliary active ingredient selected from *Betula alba* extract, a glycolipid, Bakuchiol, an anti-acne active ingredient, an antimicrobial peptide, a bacteriophage, a genetically engineered enzyme capable of degrading *P. acnes* biofilm, and combinations thereof.

22. The method of claim 21, wherein the at least one auxiliary active ingredient is selected from: an anti-acne active ingredient, a genetically engineered bacteriophage targeted for *P. acnes*, a genetically engineered bacteriophage targeted for *S. epidermis*, and combinations thereof.

23. The method of claim 17, wherein (a) comprises a phytocannabinoid-infused Pogostemon Cablin extract.

24. The method of claim 17, wherein the composition further comprises a preservative system that comprises:
   (A) from about 1 to about 5% by weight, of a *Lactobacillus* ferment;
   (B) from about 1 to about 5% by weight, of *Lactobacillus* and *Cocos nucifera* fruit extract;
   (C) up to about 0.5% by weight of salicylic acid;
   (D) up to about 0.5% by weight of at least one salt of a weak acid; and
   (E) from about 1 to about 10% by weight of propanediol, all weights based on the total weight of the composition.

25. A method of managing exaggerated sebum production in oily-prone skin, the method comprising applying onto the skin a composition that comprises:
   (1) a mixture of at least:
      (a) from about 0.02 to about 0.03% by weight of a phytocannabinoid-infused Pogostemon Cablin extract;
      (b) from about 1 to about 2% by weight of a blend of *Tetraselmis chuii* and *Fucus spiralis* algae extracts;
      (c) from about 1.5 to about 2.5% by weight of *Centella asiatica* extract; and
      (d) from about 0.02 to about 0.03% by weight of Tulsi extract;
   (2) optionally, an emulsifier;
   (3) a preservative system comprising:
      (A) from about 2 to about 4% by weight, of a *Lactobacillus* ferment;
      (B) from about 2 to about 4% by weight, of *Lactobacillus* and *Cocos nucifera* fruit extract;
      (C) from about 0.25 to about 0.4% by weight, of salicylic acid;
      (D) from about 0.2 to about 0.4% by weight of potassium sorbate; and
      (E) from about 4 to about 6% by weight of propanediol, wherein all weights are based on total weight of the composition;
   (4) a dermatologically acceptable carrier; and
   (5) optionally, at least one auxiliary ingredient selected from *Betula alba* extract, a glycolipid, Bakuchiol, an anti-acne active ingredient, an antimicrobial peptide, a bacteriophage, a genetically engineered enzyme capable of degrading *P. acnes* biofilm, and combinations thereof,
   wherein the composition has a pH ranging from about 4.5 to about 5.5.

26. The method of claim 25, wherein the auxiliary ingredient is selected from: an anti-acne active ingredient, a genetically engineered bacteriophage targeted for *P. acnes*, a genetically engineered bacteriophage targeted for *S. epidermis*, and combinations thereof; optionally wherein the anti-acne ingredient is selected from salicylic acid, sulfur, a fruit acid, gluconolactone, and combinations thereof.

27. The method of claim 17, wherein the mixture of (1) further comprises from about 0.01 to about 0.05% by weight of an extract of Tulsi.

28. The method of claim 22, wherein the anti-acne active ingredient is selected from salicylic acid, sulfur, a fruit acid, gluconolactone, and combinations thereof.

29. The method of claim 17, wherein (a) is employed in an amount of from about 0.02 to about 0.05% by weight, (b) is employed in an amount of from about 0.5 to about 2.5% by weight, and (c) is employed in an amount of from about 1.0 to about 3.0% by weight.

\* \* \* \* \*